United States Patent [19]

Guyette

[11] E Re. 28,674

[45] Reissued Jan. 6, 1976

[54] CATAMENIAL DEVICE

[76] Inventor: Linda S. Guyette, 35 Summer St., Rutland, Vt. 05701

[22] Filed: Oct. 12, 1973

[21] Appl. No.: 405,766

Related U.S. Patent Documents

Reissue of:

[64] Patent No.: 3,732,866
Issued: May 15, 1973
Appl. No.: 116,531
Filed: Feb. 18, 1971

[52] U.S. Cl. ..... 128/285; 128/270
[51] Int. Cl. ..... A61f 13/20
[58] Field of Search ..... 128/270, 285, 296, 263

[56] References Cited

UNITED STATES PATENTS

| | | | |
|---|---|---|---|
| 1,222,825 | 4/1917 | Walter | 128/285 X |
| 1,401,358 | 12/1921 | Peterkin | 128/270 |
| 1,887,526 | 11/1932 | Spielberg et al. | 128/270 |
| 3,085,574 | 4/1963 | Penska | 128/263 |

FOREIGN PATENTS OR APPLICATIONS

| | | | |
|---|---|---|---|
| 1,007,643 | 2/1952 | France | 128/285 |

*Primary Examiner*—Aldrich F. Medbery
*Attorney, Agent, or Firm*—Kenway & Jenney

[57] ABSTRACT

An improvement in a tampon for absorbing menstrual fluids in which a capillary wick of non-absorbing material extends into the interior body of the tampon. The wick acts as a capillary transport to carry fluids to the core of the tampon body, thus using the absorptive capacity of the unexposed cotton.

17 Claims, 2 Drawing Figures

CATAMENIAL DEVICE

Matter enclosed in heavy brackets [ ] appears in the original patent but forms no part of this reissue specification; matter printed in italics indicates the additions made by reissue.

My invention relates to intravaginal catamenial devices and relates more particularly to an improvement in such devices whereby they are made much more effective as absorbing mediums for menstrual fluids.

Devices in common use today come in a number of variants. However, they all essentially comprise a compressed cylinder of cotton. The cotton is preferably highly absorbent, but must be densely packed for efficient use. The cotton cylinder is usually contained in a rigid plastic applicator tube, although the structural integrity of the cylindrical shape is dependent on the compressing process, and not upon said tube.

When inserted in the vaginal cavity, a cord (stitched to the cotton) extends therefrom, and provides the means for removal after use. Appearance of menstrual blood on the cord is an indication to the user that no further effective absorption can be expected from the device. The need for its removal and replacement is thus indicated.

I have found that a significant portion of the absorptive capacity of the cotton is never used. After the top end of the dense cotton cylinder has been wetted, the fluids run down along the outside surface of the cylinder. The cotton, of course, absorbs the fluids, but it is only the surface cotton (and then only to a limited depth) that is actually effective. A significant portion of the cotton at the core of the cylinder (as much as 40 percent to 60 percent) remains dry. This is for two basic reasons: the cotton is densely packed; also once the surface is wet, the cotton is a poor conducting medium for any further transfer of fluid to the center. At this point, the indication for removal appears and the device, only partially used, must be discarded.

I solve this problem by adding a transporting element to carry menstrual fluids to the interior of the cotton cylinder whereby 90 percent or more of the cotton is effectively used, thus significantly extending the life of each replacement.

Figure 1:
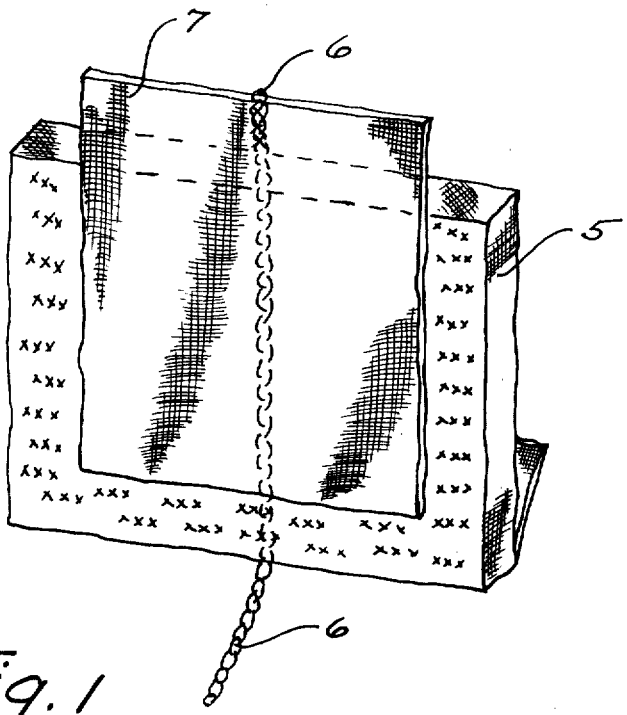
Figure 2:
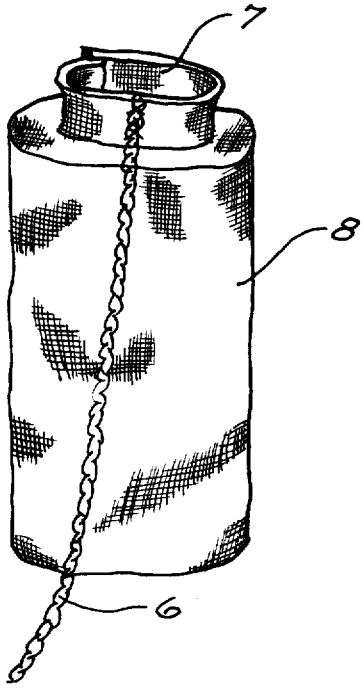

For a complete understanding of my invention, refer to the accompanying drawing in which FIG. 1 is an exploded view of the tampon as it appears before compression, with the element of the invention added; and FIG. 2 is the tampon after compression and ready for use.

Referring now more particularly to the drawing, a block of cotton is provided in accordance with present practice. A removal cord 6 is stitched to the cotton mass on the back side (as shown). The front side may be called the thread side. The thread side is the surface which becomes the interior portion of the cylinder of FIG. 2.

To the thread side of the cotton I affix by stitching a capillary wick 7. It will be appreciated that this device is mass produced; the thread stitching, the cord 6 and the wick 7 are all affixed to the cotton mass by suitable machinery in one pass. The wick 7 is preferably made of a non-absorbing synthetic material which is porous; the interstices form capillary avenues through which fluids are transported. The wick 7 is flexible (as a fabric) and I have found a wide variety of substances in the nylon or rayon class to be effective. Certain fiber glass woven materials may also be used. The important point is that the wick itself does not become saturated by absorption, but continues to act as a capillary transport delivering fluid to the interior cotton, where it is absorbed and retained.

The wick 7 is positioned to extend beyond what will be the top end of the tampon, while the bottom end stops before the lower edge of the cotton block as shown.

When compressed, the completed tampon 8 is shown in FIG. 2. The wick 7 extends in the order of one-fourth of an inch or so from the top end of the tampon 8 and leads into the interior of the cotton cylinder.

In use, the menstrual fluids are not only absorbed by the surface cotton as is now the case, but they migrate from the top by capillary action through the wick 7 into those interior portions of the cotton that heretofore have remained dry. Thus the effective capacity of the tampons now in general use is greatly increased.

While I have shown a particular embodiment of my invention for purposes of illustration, it will be appreciated that the inventive concept can easily be applied to any of a variety of tampons now on the market. For example, the cotton block 5 may be in a wide range of dimensions. In some cases the mass is rolled to form the final cylindrical shape, in which case alternate layers of wick and cotton are formed along a radial line of the cylinder. I have shown a method of construction easily adapted to present production techniques. However, the wick material could be introduced between two layers of cotton, to make a "sandwich" which could then be either rolled or crushed into final form. The particular method of assembly may be chosen to suit the machinery which it is desired to use. I therefore include all variations as will occur to persons skilled in the art which are within the spirit and scope of the following claims:

I claim:

1. A rolled cylindrical tampon *having means for conducting body fluid to the interior thereof, said tampon* comprising a first sheet of absorbent material, *and* a second sheet of [non-absorbtive] *relatively non-absorbent wick-like* synthetic woven material superimposed on one face of said first sheet and extending beyond at least one edge of said first sheet, *said first and second sheets being rolled into a cylinder having its outer cylindrical surface formed by a portion of said first sheet and having the non-extending portion of said second sheet disposed entirely within said outer surface,* [whereby] *so that* upon rolling said [sheet] *sheets* into a cylinder said second sheet [will act as] *forms* a spiral wick to the interior of said cylinder.

*2. In an intravaginal tampon, the combination of first means for absorbing menstrual fluid and having an outer body of material absorbent to such fluid and with top and bottom ends, and second means for transporting menstrual fluid from said top end of said tampon body directly into the interior of said body, said second means comprising a relatively non-absorptive wick element disposed within and in contact with the interior of said outer body and extending from said top end thereof.*

*3. In a tampon as defined in claim 2, the further improvement wherein said wick element is constructed of a material substantially nonabsorbent to such menstrual fluid.*

*4. In a tampon as defined in claim 3, the further improvement wherein said wick element is structured to pass menstrual fluid therethrough by capillary action.*

*5. In a tampon as defined in claim 4, the further improvement in which said wick element is a woven synthetic material having interstices which form capillary avenues for transportation of such menstrual fluid.*

*6. In a tampon as defined in claim 2, the further improvement wherein said wick element protrudes beyond said body of absorbent material at said top end thereof.*

*7. In a tampon as defined in claim 6, the further improvement wherein said wick element is constructed of a material substantially nonabsorbent to such menstrual fluid.*

*8. In a tampon as defined in claim 7, the further improvement wherein said wick element is structured to pass menstrual fluid therethrough by capillary action.*

*9. In a tampon as defined in claim 8, the further improvement in which said wick element is a woven synthetic material having interstices which form capillary avenues for transportation of such menstrual fluid.*

*10. In a tampon as defined in claim 2, the further improvement wherein said wick element extends within the interior of said body from the top end thereof in the direction toward, but only part of the distance to, the bottom end thereof.*

*11. An intravaginal catamenial tampon comprising*

*A. an outer member including a body of material absorbent to menstrual fluids, and having opposed top and bottom ends and outside surfaces therebetween, and*

*B. an inner member including a relatively nonabsorbent fluid-transporting element for carrying menstrual fluids to the interior of said body from said top end thereof, said transporting element being in contact with said body and disposed within the interior of said body from said outside surfaces and extending from only the top end thereof.*

*12. A tampon as defined in claim 11 further characterized in that said transporting element is of a material substantially nonabsorbent to such menstrual fluids and is structured for transporting such fluid therethrough by capillary action.*

*13. A tampon according to claim 12 further characterized in that said transporting element is woven of synthetic material and has interstices which form capillary menstrual fluid-transporting avenues.*

*14. A tampon according to claim 11 further characterized in that said transporting element protrudes beyond said body of absorbent material at said top end thereof.*

*15. A tampon as defined in claim 14, further characterized in that said transporting element is of a material substantially nonabsorbent to such menstrual fluids and is structured for transporting such fluid therethrough by capillary action.*

*16. A tampon according to claim 15 further characterized in that said transporting element is woven of synthetic material and has interstices which form capillary menstrual fluid-transporting avenues.*

*17. A tampon according to claim 11 further characterized in that said transporting element extends within the interior of said body from the top end thereof in the direction toward, but only part of the distance to, the bottom thereof.*

* * * * *